United States Patent
Fenton, Jr.

(10) Patent No.: US 6,409,743 B1
(45) Date of Patent: Jun. 25, 2002

(54) DEVICES AND METHODS FOR SECURING SUTURES AND LIGATURES WITHOUT KNOTS

(75) Inventor: Paul V. Fenton, Jr., Marblehead, MA (US)

(73) Assignee: Axya Medical, Inc., Beverly, MA (US)

( * ) Notice: Subject to any disclaimer, the term of this patent is extended or adjusted under 35 U.S.C. 154(b) by 0 days.

(21) Appl. No.: 09/349,663

(22) Filed: Jul. 8, 1999

Related U.S. Application Data (60) Provisional application No. 60/092,073, filed on Jul. 8, 1998, and provisional application No. 60/092,074, filed on Jul. 8, 1998.

(51) Int. Cl.⁷ .............................................. A61B 17/04
(52) U.S. Cl. ...................................................... 606/232
(58) Field of Search ................................. 606/232, 144, 606/138; 29/243; 24/30.5 R, 30.5 W, 30.5 P, 114.6, 17 AP, 11, 304

(56) References Cited

U.S. PATENT DOCUMENTS

| | | | |
|---|---|---|---|
| 3,503,119 A | * | 3/1970 | Seitz, Jr. et al. ............... 29/509 |
| 3,513,848 A | | 5/1970 | Winston et al. |
| 3,664,345 A | * | 5/1972 | Dabbs et al. ............... 128/335 |
| 3,802,438 A | * | 4/1974 | Wolvek ...................... 128/335 |
| 3,857,396 A | * | 12/1974 | Hardwick ................... 128/335 |
| 3,879,981 A | * | 4/1975 | Richards ...................... 72/410 |
| 3,995,870 A | * | 12/1976 | Hulek ......................... 219/58 |
| 4,050,100 A | | 9/1977 | Barry |
| 4,291,698 A | * | 9/1981 | Fuchs et al. ................ 128/335 |
| 4,588,408 A | | 5/1986 | Yamada |
| 5,078,731 A | * | 1/1992 | Hayhurst ..................... 606/232 |
| 5,356,417 A | | 10/1994 | Golds |
| 5,376,101 A | * | 12/1994 | Green et al. ................ 606/232 |
| 5,383,883 A | | 1/1995 | Wilk et al. |
| 5,383,905 A | | 1/1995 | Golds et al. |
| 5,391,173 A | * | 2/1995 | Wilk ........................... 606/144 |
| 5,413,585 A | | 5/1995 | Pagedas |
| 5,417,700 A | * | 5/1995 | Egan ........................... 606/144 |
| 5,425,489 A | | 6/1995 | Shichman et al. |
| 5,437,685 A | | 8/1995 | Blasnik |
| 5,500,018 A | | 3/1996 | Spotorno et al. |
| 5,527,341 A | | 6/1996 | Gogolewski et al. |
| 5,586,983 A | | 12/1996 | Sanders et al. |
| 5,593,425 A | | 1/1997 | Bonutti et al. |
| 5,611,801 A | | 3/1997 | Songer |
| 5,618,311 A | | 4/1997 | Gryskiewicz |
| 5,643,289 A | | 7/1997 | Sauer et al. |
| 5,732,530 A | * | 3/1998 | Pfaff ........................... 53/403 |

(List continued on next page.)

*Primary Examiner*—Jeffrey A. Smith
*Assistant Examiner*—Eduardo C. Robert
(74) *Attorney, Agent, or Firm*—McDermott, Will & Emery (57) ABSTRACT

A fusible collar for securing sutures without knots and for securing living tissue structures together without sutures is provided. The fusible collar is made of a resilient compressible material and is formed generally in a C-shape which can be compressed into an O-shape, with portions of the collar overlapping around the structures to be secured. Energy is applied to the overlapping portions of the collar to cause localized heating and plastic flow so as to fuse the overlapped portions together. The collar can include one or more energy directors on a contact surface to direct and focus energy to particular regions so as to effect collar-to-suture welding.

The invention further provides a kit for securing elongated structures without knots. The kit includes the fusible collar and a tool for compressing the collar around the elongated structures and fusing the collar to itself and/or the elongated structures. The tool includes generally an energy source; a weld head; and an end effector for supporting the collar during compression; and electronics, switches, and control devices for supplying the weld energy and activating the end effector. Suitable energy sources for welding include thermal, optical, heat, radiofrequency energy, current sources, and preferably ultrasonic energy.

46 Claims, 6 Drawing Sheets

U.S. PATENT DOCUMENTS

| | | |
|---|---|---|
| 5,735,877 A | 4/1998 | Pagedas |
| 5,766,218 A | 6/1998 | Arnott |
| 5,769,894 A | 6/1998 | Ferragamo |
| 5,881,452 A * | 3/1999 | Nowell, III et al. .......... 29/816 |
| 5,893,880 A | 4/1999 | Egan et al. |
| 5,941,901 A | 8/1999 | Egan |

* cited by examiner

DEVICES AND METHODS FOR SECURING SUTURES AND LIGATURES WITHOUT KNOTS

CROSS REFERENCE TO RELATED APPLICATIONS

This application is a continuation in part of provisional U.S. applications Ser. No. 60/092,073, and Ser. No. 60/092074, both filed Jul. 8, 1998, the disclosures of which are hereby incorporated by reference into this application.

FIELD OF THE INVENTION

The present invention relates generally to devices and methods for joining sutures together without knots, and for securing living tissue structures together without sutures.

BACKGROUND OF THE INVENTION

In minimally invasive surgical procedures that use elongated instruments and videoscopic viewing of the surgery site, there is a significant elevation in the difficulty of knot tying and wound approximating. Traditional methods of wound closure routinely involve the use of individual hand-knotted sutures. The suture strands are directed through portions of tissue to be joined and formed into a single stitch, which is then knotted. However, due to the location of the area being sutured, the delicate nature of anatomical features, and the stiffness of the suture used, it can be difficult to tie uniform stitches to close the wound that do not unravel or tie off (or ligate) a vessel. Non-uniform stitches (i.e., stitches of varying tension) or varied bite size (depth into the tissue) can cause uneven healing, localized trauma, infection, and patient discomfort.

To reduce the discomfort and aid healing, it is desirable to secure sutures uniformly and close to a wound. Due to the stiffness of some sutures, knotting the sutures can be difficult, particularly when the tissue to be sutured is deep within the body. Typical knots may be relatively large and elevated above the tissue being sutured, which can increase patient discomfort.

It is also desirable in many surgical procedures where sutures are used to reduce the size of the knot bundle and the amount of foreign material in the body. The knot bundle can become an irritant and retard the healing process and cause discomfort or pain for the patient. The knot bundle can also be a source of infection.

Methods known in the art to overcome these problems include various suture securing devices such as buttons, and methods of fusing synthetic sutures. Although buttons can produce sutures with even tension and without the concomitant dexterity of knot tying, their elevated location above the wound or within the body cavity can cause irritation and discomfort. Furthermore, there is a risk of button migration, since they are discrete objects in the body.

Suture fusion techniques, whereby synthetic polymer suture strands are melted together by the application of heat or other energy to the sutures, are known in the art. Examples of devices to perform such suture fusion are disclosed in U.S. Pat. No. 5,417,700, assigned to the assignee of this application and incorporated herein by reference. However, some polymeric sutures are not amenable to this process. For example, braided or multi-filament sutures may not completely fuse since spaces between the individual strands may interfere with the heat or energy transfer needed for fusion to occur. As a result, the sutures may be incompletely fused, and the resulting joint may fail.

It would be advantageous to provide suture and tissue joining devices which are fusible to and/or around sutures and other structures, including living tissue, so as to avoid the need for suture knots.

SUMMARY OF THE INVENTION

According to one aspect of the invention, there is provided a device for securing one or more elongated members or the same elongated member looped upon itself. The device is a flexible, fusible collar that is disposed about a central region which extends about a central axis. The collar extends circumferentially between two end portions and is biasable into a nominally closed position so that the end portions of the collar overlap. In this form the collar is adapted to encircle a portion of the elongated members. The overlapping portions of the collar are adapted to fuse to each other around the elongated members upon application of sufficient energy to the overlapping portions of the collar.

In one embodiment, the elongated members are surgical sutures which are made of a fusible material. The sutures are adapted to fuse at least to each other and possibly also to the collar in a knotless weld upon application of sufficient energy to the collar.

In another embodiment, the sutures are made of non-fusible, or minimally fusible material and only the collar is providing the welded interface. In another embodiment, the sutures are made of braided material that is marginally fusible. In another embodiment, the elongated members are a band of material that encircles a bundle of other structures, such as blood vessels.

The collar is preferably made of a thermoplastic polymeric material. The elongated members can be surgical sutures which are also made of a fusible, thermoplastic polymeric material. In another embodiment, the elongated members can be living tissue structures. The energy may be generated from a variety of sources known in the art, such as for example, thermal energy, optical energy, radio-frequency energy, current sources or more preferably, ultrasonic energy.

In a preferred embodiment, the collar includes one or more energy directors extending from a surface of the collar. The energy directors define fusion regions of the sutures and the collar and are adapted to focus energy applied to the collar to the fusion regions so that the sutures and collar fuse together preferentially at the fusion regions. The energy directors can be located along the inner surface of the collar, at the opposing surfaces of the overlap region, or both.

The inside surface of the collar may also be smooth, or have protrusions, grooves or other texturing to aid in securing the encircled structures.

According to another aspect of the invention, there is provided a kit for securing one or more elongated living tissue structures. The kit includes a fusible collar as described above, and a fusing tool which compresses the collar around the tissue structures so that the tissue structures are securely retained within the collar and portions of the collar overlap. The fusing tool applies energy to the collar to fuse the overlapped portions of the collar together around the tissue structures. The fusing tool includes generally an energy source, a welding head, an end effector, and general electronics, switches, control devices and the like for supplying weld energy and activating the end effector.

In one embodiment of the fusing tool, the energy source is ultrasonic energy. The fusing tool preferably includes an ultrasonic transducer, an ultrasonic welding horn, and an end effector. The end effector may include one or more jaw members adapted for selective deployment around at least a portion of the collar to form an ultrasonic welding anvil. In various embodiments, the end effector can be a pair of opposable jaws which move with respect to each other, or a pair of jaws which are resiliently biased toward each other.

In alternate embodiments, energy for bonding is supplied by thermal energy (e.g., heat), optical energy (e.g., laser generated), electrical energy (e.g., radio frequency, RF), or current sources (e.g., resistive heating).

According to another aspect of the invention, there is provided a kit for joining a plurality of surgical sutures together without a knot. The kit provides a fusible collar as described above, and a fusing tool as described above, for compressing the collar around the sutures so that the sutures are securely retained within the collar. The fusing tool applies energy to the collar to fuse the overlapping portions of the collar to each other and may also fuse portions of the collar to portions of the sutures.

According to yet another aspect of the invention, there is provided a method for securing one or more elongated members, such as living tissue structures. A fusible collar as described above is provided. The collar encircles the elongated members to be secured, and the collar is then compressed around the elongated member or members so that portions of the collar overlap. Energy is applied to the overlapped portions of the collar while it is compressed so that the overlapped portions are fused together around the elongated structures. The method further provides that when the living tissue structure is a blood vessel or duct, the structure is compressed within the collar so that fluid passage through the structure is impeded.

A method of joining surgical sutures together in a knotless weld comprises the steps of providing a fusible collar as described above, and encircling the sutures to be joined with the collar. The collar is then compressed around the sutures to retain them securely and to cause portions of the collar to overlap. Energy is applied to the overlapped portions of the collar to fuse those portions together, as well as to fuse portions of the collar to portions of the sutures.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

Like features in the figures are labeled with like numerals.

DESCRIPTION OF THE PREFERRED EMBODIMENTS

The present invention provides, in one aspect, a device, kit, and method for securing sutures or anatomical features in human or animal tissue that eliminates the need for tying knots in sutures. The invention is practiced with the aid of a tool that joins a fusible banding device or collar to itself around the sutures or around living tissue structures, such as ligaments, vessels and ducts. Alternatively, the collar can be fused to itself around a number of sutures, which can also be fused to one another. The devices and methods of the invention secure a fusible collar to sutures or living tissue structures close to a wound site so that the sutures can be made taut and secured without coming undone and without the bulk and inconvenience associated with knots and knotting processes, which are difficult, time-consuming and cumbersome in confined spaces. Furthermore, the joining process insures that braided and multi-filament sutures will fuse adequately and remain secure. Various methods of fusing or joining sutures or other elongated structures together joining by the application of energy to the fusible collar are well known in the art and can be employed to secure the band and sutures. Examples of such techniques include, but are not limited to, thermal energy (e.g., heat), optical energy (e.g. laser), electrical (e.g., radiofrequency RF), current sources (e.g., resistive heating), and preferably, ultrasonic energy.

Application of energy to the fusible collar may be carefully controlled, as detailed more fully below, to ensure localized melting and joining of the collar without causing trauma to underlying and nearby tissue structures.

In a preferred form of the invention, the collar is formed as a split, or open, ring-like structure which is made of a biocompatible, flexible material that is adapted to allow sutures, and/or other anatomical structures (vessels, ducts, ligaments and the like) to be encircled by it. The collar may be resilient or substantially resilient so that after cessation of a deforming force, it returns to substantially its original shape. The collar can be made in various geometries and may have one or more energy directors extending from a surface of the collar to focus energy propagating through the collar at particular areas, or fusion regions, on the collar. Such fusion regions may be regions of contact between the collar and sutures contained therein, so that fusion occurs preferentially at those regions during compression of the collar and application of energy thereto.

Throughout the specification, it will be understood that the collar can be used to encircle living tissue structures and cinch or bundle them together, wherein the collar is then fused to itself at an overlap region to secure the bundled structures together. Similarly, the collar can encircle one living tissue structure, such as a blood vessel or duct, then fuse to itself in a manner that restricts the flow of fluid through the structure (ligate). Alternatively, the collar can be used to encircle and secure a plurality of fusible surgical sutures, which can themselves be melted and fused together, and optionally to the collar, upon application of energy to the collar.

Figure 1:
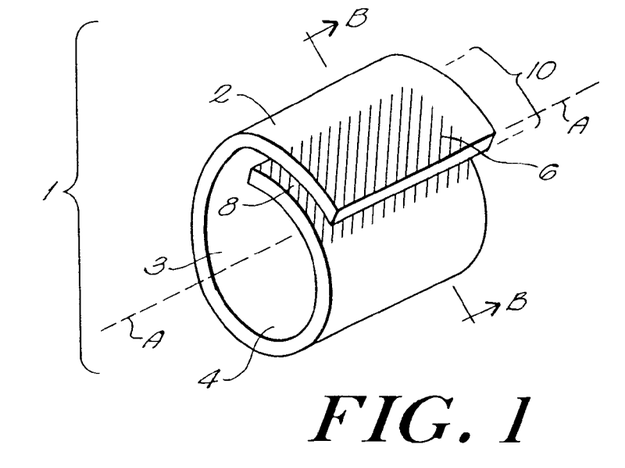
FIG. 1 is an oblique view of a preferred embodiment of the collar of the invention.

FIG. 1 shows one embodiment of the collar 1 which is formed substantially as a "c" -shape and which is resiliently biased into a nominally closed "o"- shaped position so as to encircle a generally cylindrical central region 3 extending along central axis A for retaining sutures or living tissue structures. End portion 6 extends circumferentially and overlaps end portion 8 at overlap area 10 to form a tubular structure.

Central region 3 of the tubular structure should be large enough to permit the sutures or tissue structures to be secured therein by the collar so that the its end portions 6, 8 overlap. The inner surface 4 of the collar can be smooth, or it can be grooved, have protrusions, or be otherwise textured in some way, to create a roughened surface area to enhance contact between the collar and the structure(s) therein. This latter form is particularly useful when securing a collar to a tissue such as a ligament.

Figure 2A:
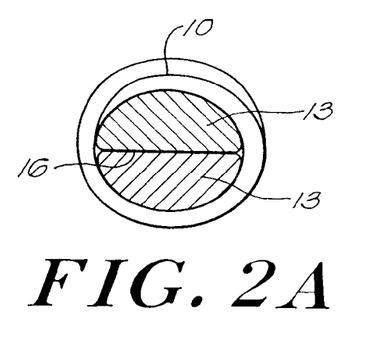
FIG. 2A is a cross-sectional view of a fused collar around a pair of suture strands, taken along section lines B—B of FIG. 1.
Figures 2B, 3A:
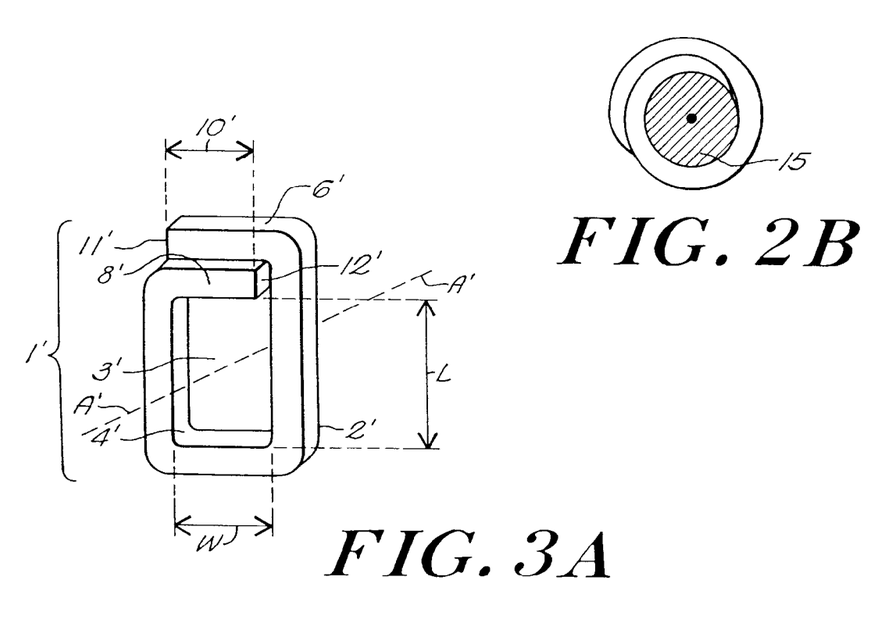
FIG. 2B is a cross sectional view of a fused collar around a tubular structure such as a vessel, taken along section lines B—B of FIG. 1.
FIG. 3A is an oblique view of another preferred embodiment of the collar.

FIG. 2A shows the collar after it has been compressed so that end portions 6, 8 overlap. Following the compression, collar 1 is fused around a pair of sutures 13. Preferably, collar 1 is compressed around the sutures 13, so that the sutures are pressed against each other to the point of deformation, thereby increasing their mutual contact surface areas. FIG. 2B shows the collar compressed around and ligating an anatomical structure, such as a blood vessel 15.

Depending on the selection of materials for the collar and the sutures, fusion can occur in selected regions, i.e., in the overlap region 10 of the collar, between the collar and the sutures at energy directors, discussed more fully below, and at interface regions 16 between the sutures themselves.

Figure 3B:
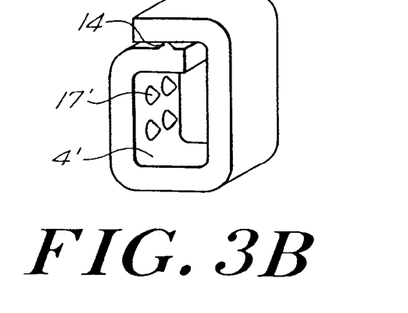
FIG. 3B is an oblique view of another preferred embodiment of the collar displaying a modified inner surface.

FIGS. 3A and 3B show the details of alternate embodiments of the collar 1'. In FIG. 3A, collar 1', like collar 1, is fashioned from a flexible, biocompatible material. Collar 1' is also formed in substantially a "c" shape, albeit with a squared shape forming central region 3' about a central axis A' for retaining the structures. In this embodiment, central region 3' may have length (L) and width (W) forming substantially a rectangular shape. In a preferred embodiment, W is approximately equal to or slightly larger than the diameter of one structure to be secured therein; length L is approximately equal to or greater than the diameter of two structures to be secured therein. This dimensioning of the collar maintains the sutures or ligaments therein in a preferred alignment with the welding horn during the fusing process, thereby providing for optimal transmission of the bonding energy to the contact areas. Other dimensions for the collar in this example are considered to be within the scope of the invention.

To form the tubular fused structure, end portion 6' overlaps end portion 8' at overlap area 10'. Longitudinally running edge 12' on the end portion 8' may be in contact with inner surface 4' or spaced apart from inner surface 4' to give the collar an open, or "c", shape. Inner surface 4' may be smooth, or it can be grooved, or have protrusions or be otherwise textured to enhance engagement of the sutures and collar for efficient fusing or welding. FIG. 3B shows a collar 1' which is similar to the collar in FIG. 3A, except that it has cone-shaped protrusions 17' extending inwardly from inner surface 4'. Other shapes for protrusions may be used.

To permit attached tissue structures to be encircled by collar 1', end portions 6' and 8' may be eased apart in opposite directions so as to admit and encircle the structures. Alternately, sutures or non-attached structures may be threaded through the central region 3' of the collar.

Figure 4:
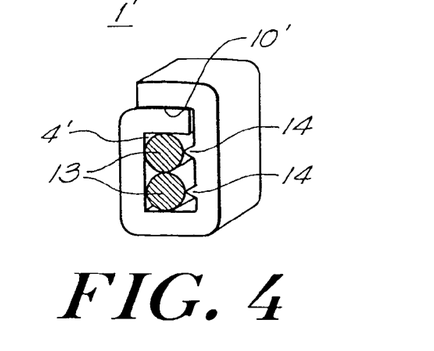
FIG. 4 is an oblique view of yet another embodiment of the collar.

An alternate embodiment of the collar is shown in FIG. 4. This embodiment contains all the details found in the embodiment shown in FIG. 3 with the addition of one or more energy directors 14 located on a contact surface, illustrated here as inner surface 4'. The energy directors 14 focus the applied energy at particular points, or fusion regions, for example, at the junction between the sutures and inner surface of the collar or on the opposing surfaces of the end portions at the overlap area. The energy directors insure that welds are formed preferentially at these locations.

The collar is preferably made of a biocompatible material which is sufficiently flexible to allow for moderate deformation of the collar to allow sutures or other anatomical structures to be placed within the collar. The collar may be substantially resilient so that after cessation of a deforming force, it returns substantially to its original shape around the sutures or structures therein. In one form, the material is resilient so as to retain the structures within the collar and create contact surfaces or fusion regions for the welds. Any type of material that meets these requirements can be used.

The collar material is preferably also capable of being fused or joined together upon the application of energy, such as thermal energy (heat), optical energy (laser generated), electrical energy (radio frequency, RF), current sources (resistive heating) or, preferably, ultrasonic energy, to the collar. Preferred materials are synthetic polymers capable of being repeatedly softened or melted with the application of heat or pressure (commonly known as thermoplastics). Thermosetting plastics and other heat-fusible materials may also be suitable for use as a collar under certain conditions.

The collar can be made by methods known in the art, such as, but not limited to, machining, injection molding, extrusion, thermoforming and the like.

If desired, a collar made of one material, and sutures made of a different material having a different melting temperature, can be employed together so as to further direct the melting and fusing upon application of energy to the collar. Higher melting point materials may be preferred for the collar, particularly if braided or multi-filament sutures are used, as the bonding energy can fuse underlying fibers as well as the sutures themselves. The energy required to melt the material using the various processes and the time required for the molten material to resolidify are well known in the art.

The suture material can be of any type customarily used for sutures such as silk, but preferred materials are polymers such as PTFE, and especially preferred are thermoplastic materials, such as polyamide (nylon), polypropylene, polyester, polyglycolic acid (PGA), polyglyconate, and polydioxanone. The sutures can be either substantially monofilamentous, multiple stranded, twisted, braided, or otherwise interlinked material. The suture filament can have any cross-sectional shape, for example, substantially circular, elliptical or rectangular.

The choice of materials for the sutures and the collar and the geometry of the collar determines which materials fuse, and where fusing occurs. For example, if a collar and sutures are made from materials with largely differing melting temperatures (for example, collars are thermoset polymers or non polymer material, and the suture strands are thermoplastic polymers), the bonds can occur at the suture to suture interface, and within the individual fibers that make up the suture strand (in the case of a multi filament or braided material), but little or no fusing of sutures to the collar occurs. Conversely, when the collar is made of a thermoplastic material, and the suture is a thermoset polymer, non polymer or when an anatomical feature is within the collar, fusing of the collar to itself at the overlap areas occurs. This could be beneficial for retaining ligaments, vessels or ducts, while allowing the collar to move relative to the ligaments, vessels or ducts retained therein, or for lioating a vessel or duct. In a most preferred embodiment, the collar material and the sutures are both made of a material that melts at similar temperatures (e.g. both are thermoplastic polymers). This allow for bonds to occur at all or any of the contact interfaces described.

The fusing tool used to compress and fuse the collar generally is shown in FIGS. 5–8. The fusing tool 20 includes a shaft 22, welding head WH, and end effector 24 adapted to cradle and compress the collar around sutures or structures to be joined. The shaft also connects the welding head and end effector to various control devices 21 and electronics for receiving electrical power and converting it to weld energy, and for moving the end effector. Welding head WH transmits the weld energy to the collar.

In the ultrasonic embodiment, the welding head WH is adapted to intimately contact the surface of the collar when the collar is positioned within the end effector. End effector 24 is mounted to the shaft and surrounds the welding horn. In one embodiment, shown in FIG. 7, the end effector comprises a plurality of securing prongs, which also function as a welding anvil, and can be variously configured for use with collars of differing geometries and can be interchanged on the shaft.

Figure 5:
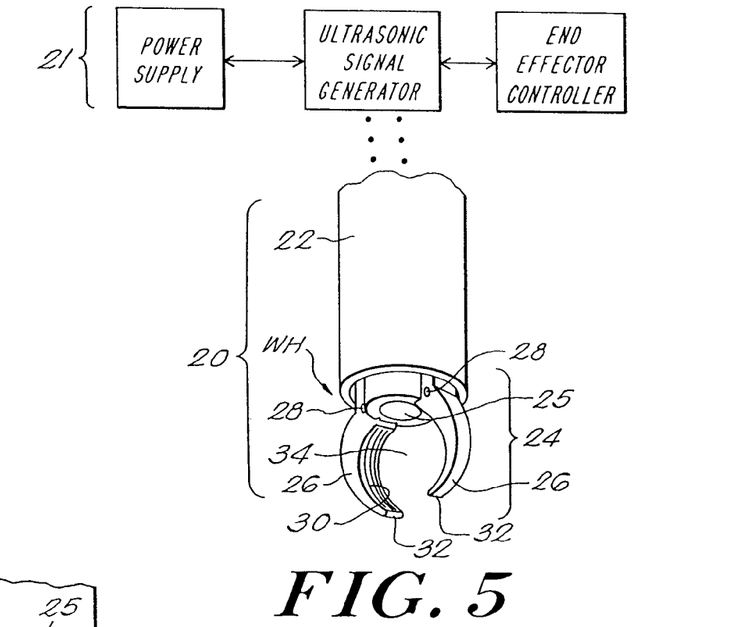
FIG. 5 is an oblique view of an end effector for a fusing tool.

FIG. 5 shows the fusing tool 20 as it appears in preparation to receive a collar. The fusing tool 20 includes a delivery shaft 22 with end effector 24 attached to the distal end of the delivery shaft at joints 28, which can be pins, hinges or the like. End effector 24 is formed by a pair of curved jaws 26 which move on joints 28 relative to each other to open and close to receive, hold and release the collar 1. Inner surfaces 30 of jaws 26 can be smooth, grooved or otherwise textured to enhance engagement between the jaws and the collar. Welding horn 25 is situated between the joints on delivery shaft 22.

Figure 6:
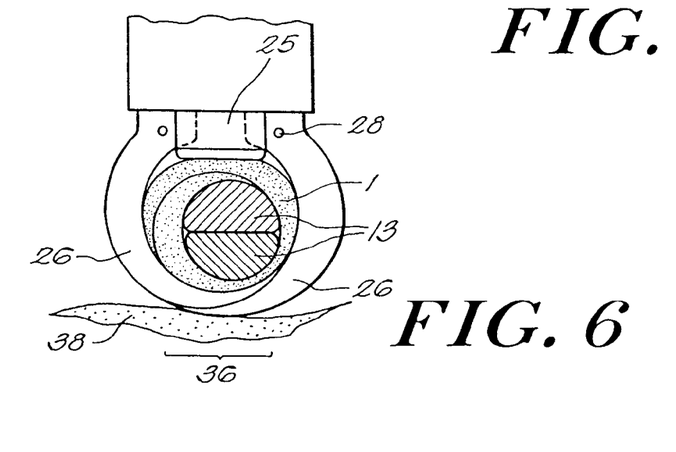
FIG. 6 is a detail view of the end effector of FIG. 5 deployed around a collar encircling sutures to be fused together.

FIG. 6 shows a fusing tool 20 with a collar 1 positioned near tissue 38 for fusing the collar around and to a pair of sutures 13. Jaw ends 32 abut or overlap to form welding anvil 36. Deployment of the jaws around the collar compresses the collar 1 around sutures 13 to maintain tension on the sutures and increase the contact surface area of the suture and collar, allowing for a larger total fused area. To fuse the collar to itself and to the sutures, bonding energy is transmitted from the welding horn 25 to anvil 36, through the collar and the sutures within the collar. The fused collar and encased sutures are released from the jaws when jaws 26 are retracted.

Figures 7, 8A, 8B:
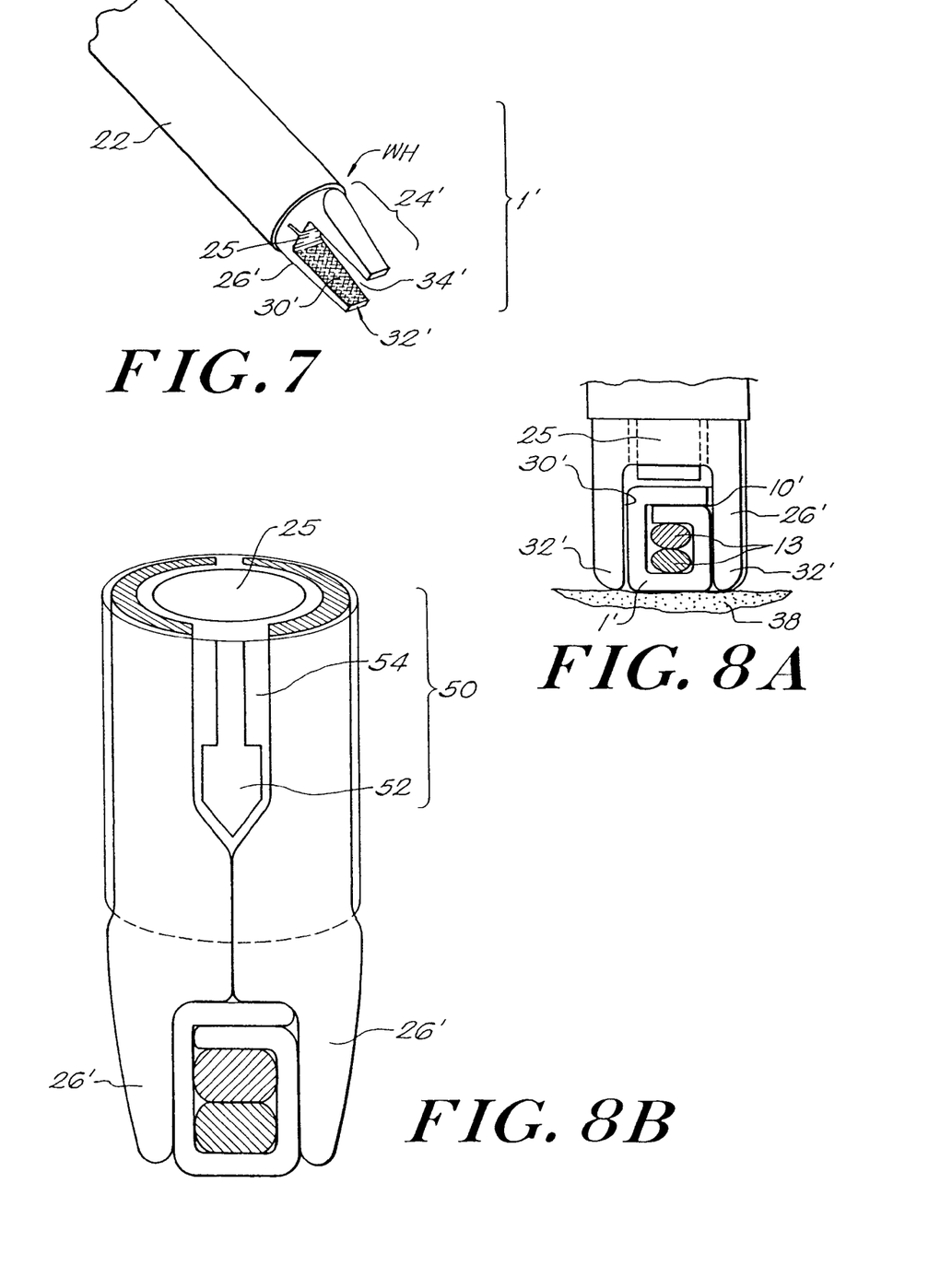
FIG. 7 is an oblique view of an alternate embodiment of an end effector for a fusing tool.
FIG. 8A is a detail view of the end effector of FIG. 7 positioned around a collar encircling sutures to be fused together.
FIG. 8B shows the cross section of the collar release mechanism for the embodiment shown in FIG. 7.

FIG. 7 shows an alternate configuration of the fusing tool 20'. In this embodiment, welding horn 25 is mounted at the distal end of delivery shaft 22 and surrounded by the end effector 24', which is formed from a plurality of resiliently mounted rigid prongs 26' extending from the shaft 22. The prongs can expand slightly to accept collar 1', and then contract to hold the collar securely and apply moderate compression to the collar and the structures within the collar.

Prongs 26' define an aperture 34' for holding collar 1' during positioning, compression and fusing of the collar and structures therein. Prongs 26' are spaced apart by sufficient distance to allow collar 1' to fit snugly yet releasably therebetween. Inner surfaces 30' of prongs 26' can be smooth, grooved or otherwise textured to enhance contact between the suture collar 1' and the prongs. Flattened or rounded ends 32' on the prongs allow for the tip to abut tissue 38 when the sutures are pulled tight through the collar, such as at a wound site, thereby minimizing any gaps in the tissue to be joined and maintaining a desired tension on the sutures. In one embodiment, the prongs can also function as an anvil. In other embodiments, underlying bone, tissue, anatomical features, or other materials temporarily or permanently placed under the end effector may also act as an anvil. The latter design may be preferable if it is necessary or otherwise advantageous to secure the collar as closely as possible to tissue so as to permit minimal gapping between the joined sutures and the collar.

FIG. 8A shows a collar and two sutures in a position to be fused. Fusing tool 20' engages collar 1' as shown. A preferred orientation is shown in FIG. 8; however, other collar orientations are within the scope of the invention. For example, the collar can be rotated so that the weld overlap area 10' is parallel to the inner surface 30' of the prongs 26'.

Prongs 26' can flex slightly to expand and accommodate the collar within aperture 34' and hold the collar snugly, yet releasably within the aperture. This moderate compression of the collar within the aperture can also further compress the sutures within the collar, increasing the contact interfaces between the sutures and the collar. This is especially preferred when braided sutures are used, as the compressive force on braided sutures reduces the volume of air spaces between the braid filaments. As the fusing tool is energized, fusing energy is transferred to the collar and sutures. Fusing may occur, for example, at the overlap area 10', between the inner surface 30' of the collar and the sutures 13, and between the suture strands themselves. Since the collar is frictionally held within the aperture 34' by the prongs 26', it can be easily removed from the opening after the weld is completed.

In an alternate embodiment, the tool includes a collar ejection mechanism 50, an example of which is shown in FIG. 8B. In this example, the injection mechanism includes one or more wedge shaped members 52, located within a recess or channel 54 in shaft, exterior to the welding horn. The release mechanism is moved downwardly toward the collar, separating prongs 26'. This separation causes a space to open between the prongs, thereby releasing the bonded collar from the assembly. Other release mechanism are also envisioned, for example, a mechanism whereby the ultrasonic horn 25 is moved downwardly into aperture 34' toward the prong ends and pushes the collar free from the prongs.

In another embodiment of the invention, the fusing tool end effector and collar comprise a kit. The kit may include various end effectors that are interchangeable on the tool shaft for accommodating different collar shapes and sizes.

A process for securing suture strands within a fusible collar is demonstrated in FIGS. 9A–9F using the collar 1 shown in FIG. 1 and the fusing tool 20 of FIG. 5. Similar procedures are used with the other embodiments. In FIG.

Figure 9A:
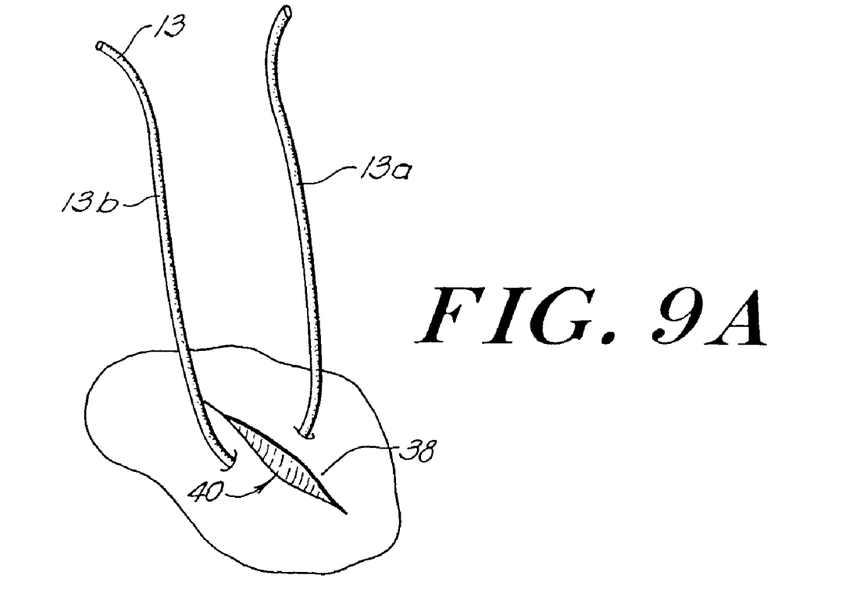
FIGS. 9A–9F are simplified diagrams of a method of securing sutures in a collar according to one aspect of the invention; shows a wound through which a suture strand has been passed.
Figure 9B:
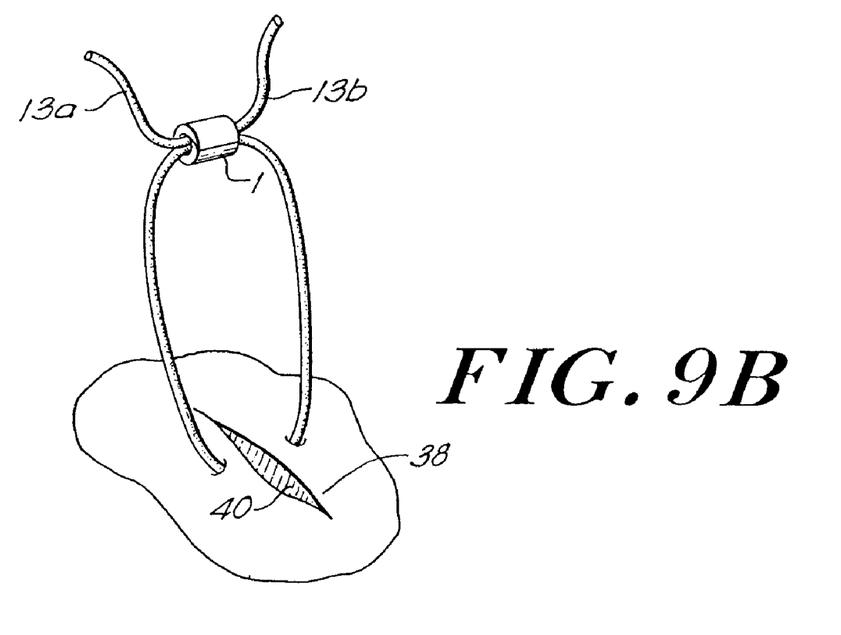
Figure 9C:
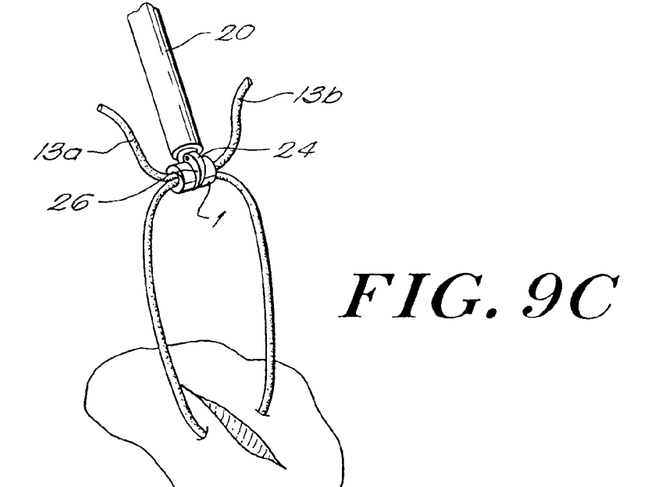
Figure 9D:
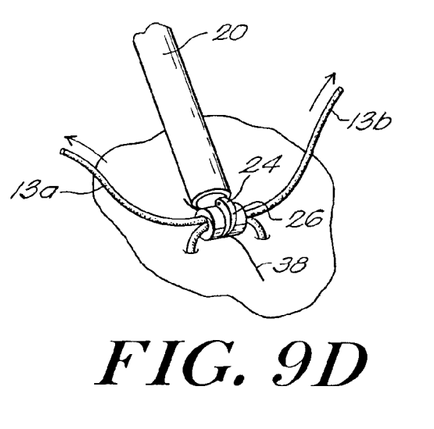
Figure 9E:
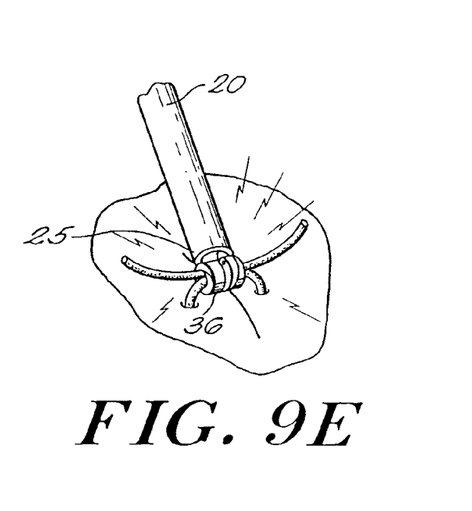
Figure 9F:
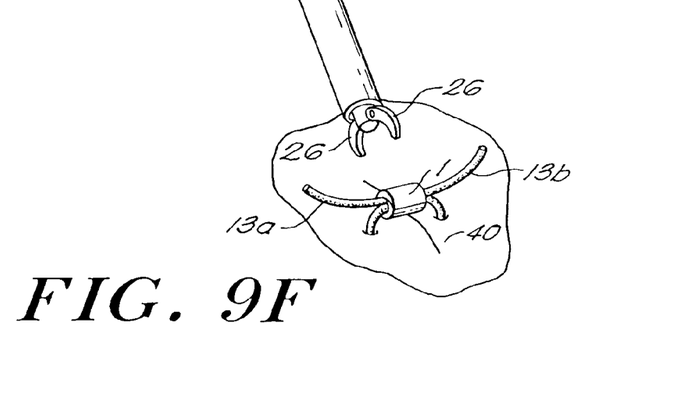

9A, a suture 13 has been passed through opening or fissure 40 in tissue 38. In FIG. 9B the suture strands 13 a,b are threaded in opposite directions through collar 1 prior to fusing. In FIG. 9C, collar 1 is engaged by the jaws 26 of the fusing tool 20. In FIG. 9D, the strands 13a,b are pulled taut in opposite directions as indicated by the arrows, thereby applying tension on opposite edges of the wound fissure 40 to close it. As shown in FIG. 9E, to secure the collar in place for welding and maintain the tension on the suture, the jaws 26 compress the collar 1 around the suture strands. Ultrasonic or thermal energy is transferred from the welding horn 25 to anvil 36 and collar 1, creating localized heat, which melts the collar 1 sufficiently to cause plastic flow and fusing of the collar to itself and to the sutures 13 encased therein. The fused collar remains within the jaws for a short period of time to allow the fused material to re-solidify. FIG. 9F shows jaws 26 retracted from the collar 1 and the fused collar-suture structure in place securing wound 40. Suture strands 13a,b can be trimmed close to the collar without loosening the fused structure.

Figure 10:
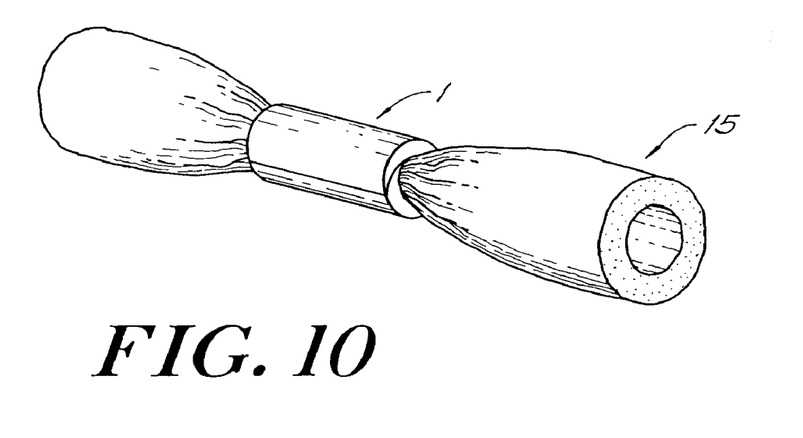
FIG. 10 is an oblique view of the collar ligating a vessel.

This method for closing a wound can be employed for other surgical procedures and anatomical structures. For example, the process for ligating a vessel or duct is similar to the one described except that the suture is threaded under or around the vessel or duct rather than throuoh tissue, and the suture is secured with an appropriate collar. Alternatively, a collar can be placed around the vessel or duct, compressed, and fused to itself. FIG. 10 shows collar 1 fused to itself around a crimped vessel 15, completing the ligation.

Figure 11A:
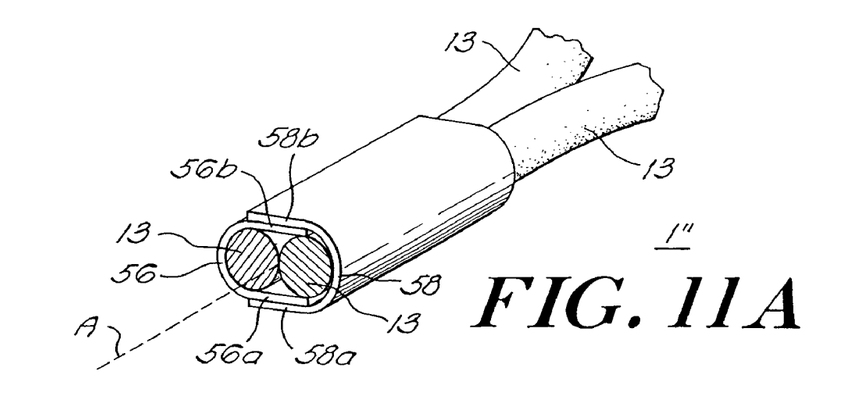
FIGS. 11A and 11B are oblique views of another embodiment of the invention.
Figure 11B:
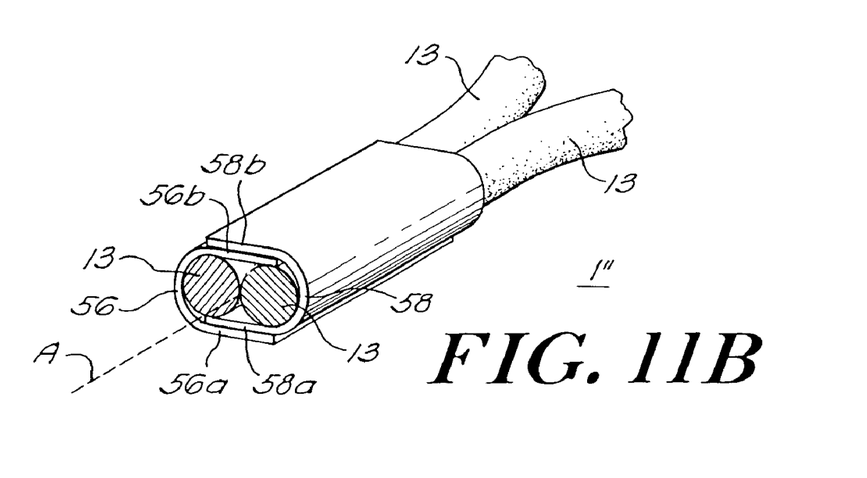

FIGS. 11A and 11B show alternate forms of the invention (collar assembly 1") which are generally similar to the embodiment of FIG. 1, but instead of a single piece structure which extends circumferentially from end portions 6 and 8, the collar assembly 1" is made of two U-shaped cross section elements 56 and 58. Element 56 extends between end portions 56a and 56b, and element 58 extends between end portions 58a and 58b. Elements 56 and 58, when connected as shown in FIGS. 11A and 11B, form a functionally similar structure to the collar 1 of FIG. 1. In use, for example, the collar assembly 1" is disposed about two sutures 13. Then, a fusing tool, for example, of the type shown in FIG. 5, is positioned about collar assembly 1", and energy is applied to effect fusion of the mutually adjacent overlapping end portions 56a, 58a, and 56b, 58b. While elements 56 and 58 are shown to have smooth, continuous cross sections from end portion to end portion, these elements, in alternate forms, may have piecewise continuous (e.g., polygonal shaped) cross sections.

Although preferred and other embodiments of the invention are described herein, further embodiments may be perceived by those skilled in the art without departing from the scope of the invention as defined by the following claims.

I claim:

1. A device for securing one or more elongated members, comprising:
    a collar having a C-shape, said collar being disposed about a central region, said central region extending along a central axis for containing at least a portion of said elongated members aligned with said central axis, wherein said collar extends circumferentially between two end portions, said collar having an innermost surface and an outermost surface, said surfaces extending between said end portions,
    said collar being resilient so that after cessation of a deforming force, said collar returns to substantially said C-shape, is made of a flexible, fusible material, and wherein said collar is deformable into a nominally closed position so that said end portions of said collar overlap so that regions of said innermost surface and said outermost surface are opposite each other forming overlapping portions, wherein the surfaces of said overlapping portions are substantially smooth and wherein the amount of overlapping is selectively adjustable and wherein said overlapping portions of said collar are adapted to fuse to each other around said central region upon application of sufficient energy to at least one of said overlapping portions of said collar.

2. The device according to claim 1, wherein the elongated members comprise surgical sutures made of a fusible material, wherein the sutures are adapted to fuse to at least one of the collar and to one another in a knotless weld upon application of sufficient energy to the collar.

3. The device according to claim 2, wherein the collar includes one or more energy directors extending from an said innermost surface of the collar into the central region, wherein the energy directors define fusion regions of the sutures and the collar and are adapted to focus energy applied to the collar to the fusion regions so that one or more of the elongated members and collar are fusible together at the fusion regions.

4. The device according to claim 1 wherein the collar includes one or more protrusions extending from said innermost surface of the collar into the central region and said protrusions are adapted to secure the elongated members within the central region.

5. The device according to claim 1, wherein the energy applied to the collar is ultrasonic energy.

6. The device according to claim 1, wherein the energy applied to the collar is selected from the group consisting of thermal energy, optical energy, electrical energy and current sources.

7. The device according to claim 1, wherein the collar is made of a thermoplastic polymeric material.

8. The device according to claim 1 where in the collar includes one or more energy directors located on one or more opposing surfaces of the end portions in the overlap area, wherein the energy directors define fusion regions for the end portions within overlapped area and are adapted to focus energy applied to the collar to the fusion regions so that the end portions are fusible together.

9. A device for securing one or more elongated members, comprising:
    a collar disposed about a central region, said central region extending along a central axis for containing at least a portion of said elongated members aligned with said central axis,
    wherein said collar extends circumferentially between two end portions, said collar having an outermost surface and an innermost surface extending between said end portions,
    wherein said collar is made of a flexible, fusible material and is deformable into a nominally closed position so that said end portions of said collar overlap so that regions of said innermost surface and said outermost surface are opposite each other forming overlapping portions, wherein the surfaces of said overlapping portions are substantially smooth and wherein the amount of overlapping is selectively adjustable, wherein said overlapping portions of said collar are adapted to fuse to each other around said central region upon application of sufficient energy to at least one of said overlapping portions of said collar, wherein the elongated members comprise surgical sutures made of a fusible material, and wherein the collar includes one or more energy directors extending from said innermost surface of the collar into the central region, wherein the energy directors define fusion regions of said surgical sutures and collar and are adapted to focus energy applied to the collar to the fusion regions so that one or more of said surgical sutures and collar are fusible together at the fusion regions in a knotless weld upon application of sufficient energy to the collar.

10. The device according to claim 9 wherein the elongated members comprise a band of material adapted for securing a plurality of anatomical structures together.

11. A device for securing one or more elongated members, comprising:

a collar disposed about a central region, said central region extending along a central axis for containing at least a portion of said elongated members aligned with said central axis, wherein said collar extends circumferentially between two end portions, said collar having an outermost surface and an innermost surface extending between said end portions, wherein said collar is made of a flexible, fusible material and is deformable into a nominally closed position so that said end portions of said collar overlap so that regions of said innermost surface and said outermost surface are opposite each other forming overlapping portions, wherein the surfaces of said overapping portions are substantially smooth and wherein the amount of overlapping is selectively adustable, wherein the collar includes one or more energy directors located on one or more opposing surfaces of the overlapping portions, said energy directors defining fusion regions for the end portions within the overlapped portions and are adapted to focus energy applied to the collar to the fusion regions so that the end portions are fusible together and around said central region upon application of sufficient energy to at least one of said overlapping portions of said collar.

12. The device according to claim 11 wherein the elongated members comprise surgical sutures made of a fusible material, wherein the sutures are adapted to fuse to at least one of the collar and to one another in a knotless weld upon application of sufficient energy to the collar.

13. A kit for securing one or more elongated living tissue structures, the kit comprising:

a collar having a C-shape, said collar being disposed about a central region, said central region extending along a central axis for containing at least a portion of said elongated members aligned with said central axis, wherein said collar extends circumferentially between two end portions, said collar having an innermost surface and an outermost surface, said surfaces extending between said end portions, said collar being resilient so that after cessation of a deforming force, said collar returns to substantially said C-shape, is made of a flexible, fusible material, and wherein said collar is deformable into a nominally closed position so that said end portions of said collar overlap so that regions of said innermost surface and said outermost surface are opposite each other forming overlapping portions, wherein the surfaces of said overlapping portions are substantially smooth and wherein the amount of overlapping is selectively adjustable, and wherein said overlapping portions of said collar are adapted to fuse to each other around said central region upon application of sufficient energy to at least one of said overlapping portions of said collar; and a fusing tool for compressing the collar around the tissue structures so that the tissue structures are securely retained within the central region, and for applying energy to the collar to fuse the overlapped portions together, wherein the fusing tool includes an energy source, a welding head for effecting the fusion, and an end effect for supporting the collar during compression and fusion.

14. The kit according to claim 13 wherein the energy source is an ultrasonic transducer, and the fusing tool further includes a welding horn extending between the ultrasonic transducer and the welding head for transmitting ultrasonic energy from the transducer to the welding head.

15. A kit according to claim 14 wherein the end effector includes one or more jaw members adapted for selective deployment around at least a portion of the collar to form an ultrasonic welding anvil.

16. A kit according to claim 15, wherein the end effector includes a pair of opposed jaws which are moveable with respect to each other.

17. A kit according to claim 15, wherein the end effector includes a pair of jaws which are resiliently biased toward each other.

18. A kit for joining a plurality of surgical sutures together without a knot, the kit comprising:

a collar having a C-shape, said collar being disposed about a central region, said central region extending along a central axis for containing at least a portion of said elongated members aligned with said central axis, wherein said collar extends circumferentially between two end portions, said collar having an innermost surface and an outermost surface, said surfaces extending between said end portions, said collar being resilient so that after cessation of a deforming force, said collar returns to substantially said C-shape, is made of a flexible, fusible material, and wherein said collar is deformable into a nominally closed position so that said end portions of said collar overlap so that regions of said innermost surface and said outermost surface are opposite each other forming overlapping portions, wherein the surfaces of said overlapping portions are substantially smooth and wherein the amount of overlapping is selectively adjustable, and wherein the overlapping portions of the collar are adapted to fuse to each other around the central region upon application of sufficient energy to at least one of the overlapping portions of the collar;

a fusing tool for compressing the collar around the surgical sutures so that the surgical sutures are securely retained within the central region, and for applying energy to the collar to fuse the overlapped portions together, wherein the fusing tool includes an energy source, a welding head for effecting the fusion, and an end effector for supporting the collar during compression and fusion.

19. A kit according to claim 18 wherein the energy source is an ultrasonic transducer, and the fusing tool further includes a welding horn extending between the ultrasonic transducer and the welding head for transmitting ultrasonic energy from the transducer to the welding head, and wherein the end effector includes one or more jaw members adapted for selective deployment around at least a portion of the collar to form an ultrasonic welding anvil.

20. A kit according to claim 19, wherein the end effector includes a pair of opposed jaws which are moveable with respect to each other.

21. A kit according to claim 19, wherein the end effector includes a pair of jaws which resiliently biased toward each other.

22. A method for securing one or more elongated members together, comprising the steps of:

provinding a collar having a C-shape, said collar being disposed about a central region, said central region extending along a central axis for containing at least a portion of said elongated members aligned with said central axis, wherein said collar extends circumferentially between two end portions, said collar having an innermost surface and an outermost surface, said surfaces extending between said end portions, said collar being resilient so that after cessation of a deforming force, said collar returns to substantially said C-shape, is made of a flexible, fusible material, and wherein said collar is deformable into a nominally closed position so that said end portions of said collar overlap so that regions of said innermost surface and said outermost surface are opposite each other forming overlapping portions, wherein the surfaces of said overlapping portions are substantially smooth and wherein the amount of overlapping is selectively adjustable, and wherein the overlapping portions of the collar are adapted to fuse to each other around the central region upon application of sufficient energy to at least one of the overlapping portions of the collar;

encircling the elongated members to be joined with the collar; compressing the collar around the elongated members so that the end portions of the collar overlap one another; and applying sufficient energy to the overlapping portions of the collar while the collar is compressed so as to fuse the overlapping portions of the collar to each other around the elongated members.

23. The method according to claim 22 wherein one elongated member is compressed by the collar to restrict the flow of fluid through the elongated member.

24. A method for joining a plurality of polymeric surgical sutures together in a knotless weld, comprising the steps of:

a collar disposed about a central recion, the central region extending along a central axis, for containing at least a portion of the polymeric surgical sutures aligned with the central axis, wherein the collar extends circumferentially between two end portions and is made of a flexible, fusible material, and wherein the collar is biasable into a nominally closed position so that the end portions of the collar overlap, and wherein the overlapping portions of the collar are adapted to fuse to each other around the central region upon application of sufficient eniergy to at least one of the overlapping portions of the collar; and encircling a plurality of surgical sutures to be joined together with the collar;

compressing the collar around the sutures so that the end portions of the collar overlap one another and contact the sutures; and applying sufficient energy to the overlapped portions of the collar while the collar is compressed around the sutures to fuse the overlapped portions of the collar to each other and portions of the collar to portions of the sutures.

25. A device for securing one or more elongated members, comprising: a collar assembly disposable about a central region, said central region extending along a central axis for containing at least a portion of said elongated members aligned with said central axis, wherein said collar assembly includes two U-shaped cross-sectioned elements, each extending between a first end portion and a second end portion and each having a innermost surface and an outermost surface extending between said end portions, wherein said U-shaped elements are adapted to interfit to extend circumferentially about said central region, with said first end portions mutually adjacent and said second end portions mutually adjacent, being made of a flexible, fusible material, and wherein said collar assembly, when interfit, is deformable into a nominally closed position so that said first end portions of said U-shaped elements overlap, and said second end portions of said U-shaped elements overlap, so that said innermost surfaces and said outermost surfaces are opposite each other forming an overlap area, wherein the surfaces of said overlapping portions are substantially smooth and wherein the amount of overlapping is selectively adjustable, and wherein said overlapping end portions of said U-shaped elements are adapted to fuse to each other around said central region upon application of sufficient energy to at least one of said overlapping portions of said collar assembly.

26. The device according to claim 25, wherein the elongated members comprise surgical sutures made of a fusible material, wherein the sutures are adapted to fuse to at least one to the collar assembly and to one another in a knotless weld upon application of sufficient energy to the collar assembly.

27. The device according to claim 26, wherein one or both U-shaped elements include one or more energy directors extending from said innermost surface of said one or both U-shaped elements into the central region, wherein the energy directors define fusion regions of the sutures and the collar assembly and are adapted to focus energy applied to the collar assembly to the fusion regions so that one or more of the elongated members and collar assembly are fusible together at the fusion regions.

28. The device according to claim 27 wherein the elongated members comprise a band of material adapted for securing a plurality of anatoimical structures together.

29. The device according to claim 25 wherein one or both U-shaped elements include one or more energy directors located on one or more opposing surfaces of the end portions thereof in the overlap area, wherein the energy directors define fusion regions for the end portions within overlap area and are adapted to focus energy applied to the collar assembly to the fusion regions so that the end portions are fusible together.

30. The device according to claim 29 wherein the elongated members comprise surgical sutures made of a fusible material, wherein the sutures are adapted to fuse to at least one of the collar assembly and to one another in a knotless weld upon application of sufficient energy to the collar assembly.

31. The device according to claim 24 wherein the collar assembly includes one or more protrusions extending from said innermost surface of one or both u-shaped elements into the central region when interfit and are adapted to secure the elongated members within the central region.

32. The device according to claim 25, wherein the energy applied to the collar assembly is ultrasonic energy.

33. The device according to claim 25, wherein the energy applied to the collar assembly is selected from the group consisting of thermal energy, optical energy, electrical energy and current sources.

34. The device according to claim 25, wherein the collar assembly is made of a thermoplastic polymeric material.

35. A device for securing one or more elongated living tissue structures, comprising:

a collar having a C-shape, said collar being resilient so that after cessation of a deforming force, said collar returns to substantially said C-shape, said collar being disposed about a central region, said central region extending along a central axis for containing at least a portion of said living tissue structures aligned with said central axis, wherein said collar extends circumferentially between two end portions said collar having an innermost surface and an outermost surface extending between said end portions, and is made of a flexible, fusible material, and wherein said collar is deformable into a nominally closed position so that said end portions of said collar overlap so that regions of said innermost and outermost surfaces are opposite each other forming overlapping portions, wherein the surfaces of said overlapping portions are substantially smooth and wherein the amount of overlapping is selectively adjustable, and wherein said overlapping portions of said collar are adapted to fuse to each other around said central region upon application of sufficient energy to at least one of said overlapping portions of said collar.

36. The device according to claim 35, wherein the collar includes one or more energy directors extending from said innermost surface of the collar into the central region, wherein the energy directors define fusion regions of the collar and are adapted to focus energy applied to the collar to the fusion regions.

37. The device according to claim 35 wherein the collar includes one or more protrusions extending from said innermost surface of the collar into the central region and are adapted to secure the living tissue structures within the central region.

38. The device according to claim 35, wherein the energy applied to the collar is ultrasonic energy.

39. The device according to claim 35, wherein the energy applied to the collar is selected from the group consisting of thermal energy, optical energy, electrical energy and current sources.

40. The device according to claim 35, wherein the collar is made of a thermoplastic polymeric material.

41. A device for securing one or more living tissue structures, comprising:

a collar assembly disposable about a central region, said central region extending along a central axis for containing at least a portion of said elongated members aligned with said central axis, wherein said collar assembly includes two U-shaped cross-sectioned elements, each extending between a first end portion and a second end portion and each having an innermost surface and an outermost surface extending between said end portions, wherein said U-shaped elements are adapted to interfit to extend circumferentially about said central region, with said first end portions mutually adjacent and said second end portions mutually adjacent, being made of a flexible, fusible material, and wherein said collar assembly, when interfit deformable into a norninally closed position so that said first end portions of said U-shaped elements overlap, and said second end portions of said U-shaped elements overlap, so that said innermost surfaces and said outermost surfaces are opposite each other forming overlap areas, wherein the surfaces of said overlapping portions are substantially smooth and wherein the amount of overlapping is selectively adjustable, and wherein said overlapping end portions of said U-shaped elements are adapted to fuse to each other around said central region upon application of sufficient energy to at least one of said overlapping portions of said collar assembly.

42. The device according to claim 41, wherein one or both U-shaped elements include one or more energy directors extending from said innermost surfaces of said one or both U-shaped elements into the central region, wherein the energy directors define fusion regions of the collar assembly and are adapted to focus energy applied to the collar assembly to the fusion regions so that the collar assembly are fusible together at the fusion regions.

43. The device according to claim 41 wherein the collar assembly includes one or more protrusions extending from said innermost surface of one or both u-shaped elements into the central region when interfit and are adapted to secure the living tissue structures within the central region.

44. The device according to claim 41, wherein the energy applied to the collar assembly is ultrasonic energy.

45. The device according to claim 41, wherein the energy applied to the collar assembly is selected from the group consisting of thermal energy, optical energy, electrical energy and current sources.

46. The device according to claim 41, wherein the collar assembly is made of a thermoplastic polymeric material.

\* \* \* \* \*